United States Patent [19]

Schwerer, III

[11] 4,215,310

[45] Jul. 29, 1980

[54] MAGNETIC TESTING METHOD AND APPARATUS HAVING PROVISION FOR ELIMINATING INACCURACIES CAUSED BY GAPS BETWEEN PROBE AND TEST PIECE

[75] Inventor: Frederick C. Schwerer, III, Franklin Township, Westmoreland County, Pa.

[73] Assignee: United States Steel Corporation, Pittsburgh, Pa.

[21] Appl. No.: 916,638

[22] Filed: Jul. 10, 1978

[51] Int. Cl.² ............................................. G01R 33/00
[52] U.S. Cl. .................................. 324/225; 324/237; 324/238
[58] Field of Search ............... 324/222, 225, 226, 228, 324/229, 233, 238–243

[56] References Cited

U.S. PATENT DOCUMENTS 3,422,346  1/1969  Hammer ................................ 324/233

OTHER PUBLICATIONS

C. V. Dodd, "A Portable Phase Sensitive Eddy Current Instrument," Material Evaluation, Mar. 1968, pp. 33–36.

*Primary Examiner*—Rudolph V. Rolinec
*Assistant Examiner*—Walter E. Snow
*Attorney, Agent, or Firm*—Walter P. Wood

[57] ABSTRACT

A method and apparatus for electromagnetic testing of magnetic and/or electrically conductive materials. The apparatus includes the usual test probe which carries excitation and pickup coils and is placed against a test piece of magnetic and/or electrically conductive material. The invention eliminates inaccuracies in the test caused by variable distances or gaps between the probe and test piece surface. Properties of the test pieces are determined by applying a controlled alternating drive current to the excitation coil so as to produce a predetermined a-c voltage in the pickup coil and measuring the drive current applied to the excitation coil when the time-integral of the voltage induced in the a-c pickup coil corresponds to zero magnetic flux in the gaps.

9 Claims, 3 Drawing Figures

MAGNETIC TESTING METHOD AND APPARATUS HAVING PROVISION FOR ELIMINATING INACCURACIES CAUSED BY GAPS BETWEEN PROBE AND TEST PIECE

This invention relates to an improved method and apparatus for electromagnetic testing of magnetic and/or electrically conductive materials.

Conventional instruments for electromagnetic testing of steel, other magnetic materials, or other electrically conductive materials include a test probe which carries a primary excitation coil and a secondary pickup coil. The probe is placed against a test piece of magnetic or electrically conductive material and the excitation coil is energized with an alternating current to establish a magnetic flux through the probe and test piece. The usual practice is to determine one or more characteristics of the voltage induced in the pickup coil—for example, voltage amplitude, phase, r.m.s. value, in-phase component, quadrature component—to monitor various properties of the test piece. (In some instruments the excitation and pickup functions are performed by a single coil.) The test is useful, for example, in monitoring differences in chemical composition, microstructure, mechanical properties, or thickness of test pieces, and also in detecting flaws. Instruments of this type are available commercially from several manufacturers, among which are Hentschel Instruments, Inc., Ann Arbor, Mich., K. J. Law Associates, Inc., Detroit, Mich., Nortec Corporation, Richland, Wash., Magnaflux Corporation, Chicago, Ill., and Krautkramer-Branson, Inc. (Magnatest), Stanford, Conn.

Unavoidably there are gaps between the end faces or poles of the probe and the surface of the test piece. Such gaps result, for example, from irregularities in the surfaces of the poles and test piece or from the presence of scale or other substances between the surfaces. Gaps in the magnetic circuit formed by the probe and test piece diminish the magnetic field intensity in the probe and test piece and thus alter the characteristics of the voltage induced in the pickup coil. The effect of gaps is quite variable, since different test pieces have different surface irregularities or carry different thicknesses of scale or the like. The usual practice of analyzing voltage induced in the pickup coil provides no compensation for inaccuracies in the test caused by variable gaps.

An object of the present invention is to provide an improved electromagnetic testing method and apparatus which eliminate inaccuracies in the test caused by gaps between the surfaces of the poles and test piece.

A more specific object is to provide an improved electromagnetic testing method and apparatus in which the drive current in the excitation coil is controlled to produce a predetermined voltage in the pickup coil and in which the drive current is measured at points in the cycle of the time-integral of the a-c voltage induced in the pickup coil corresponding with the condition of zero magnetic flux in the gaps.

Figure 1:
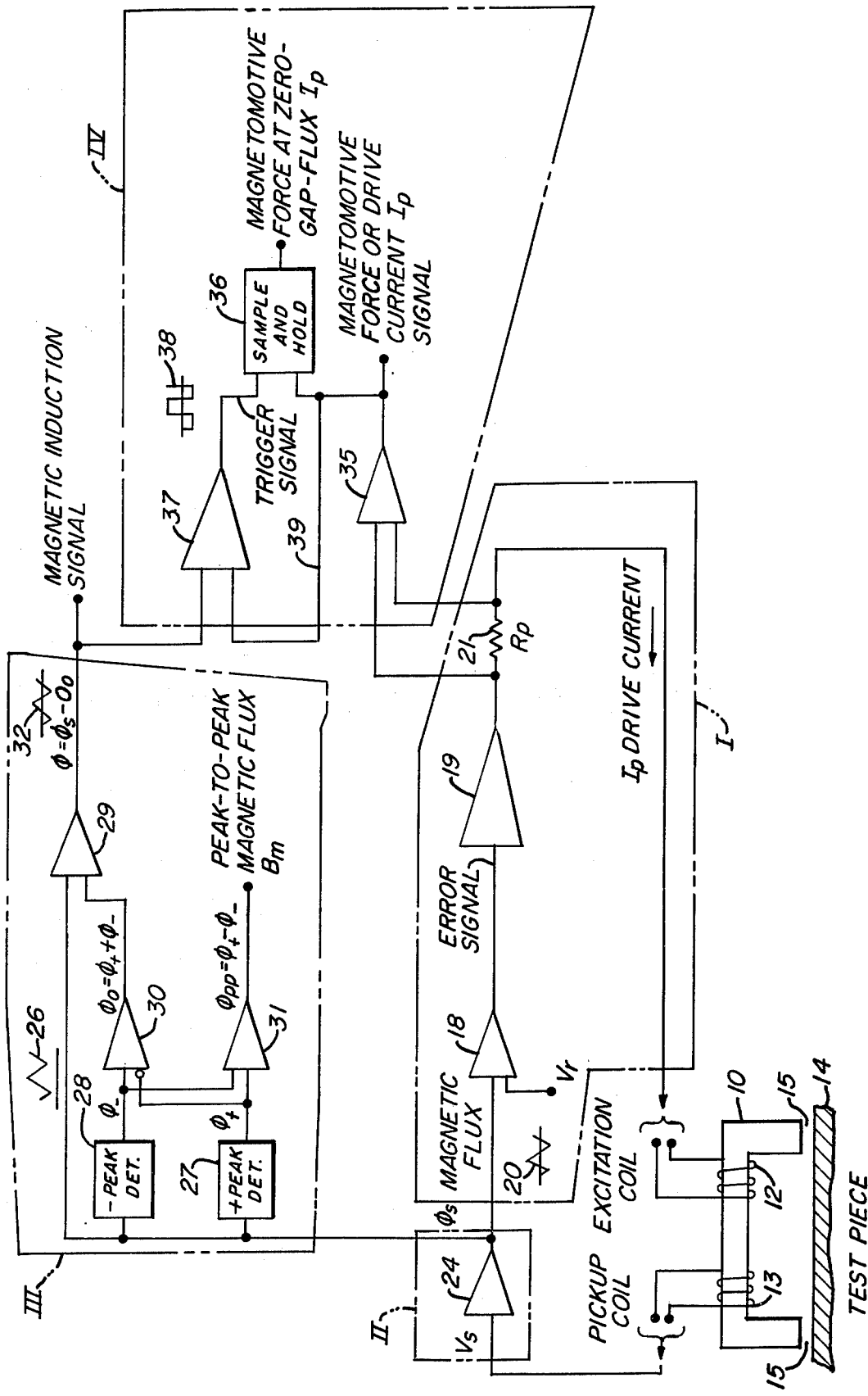
FIG. 1 is a schematic diagram which shows a conventional electromagnetic test probe, a test piece, and an example of a circuit arranged in accordance with the present invention.

FIG. 1 shows a diagrammatically a conventional electromagnetic test instrument which includes a double-pole probe 10 and excitation and pickup coils 12 and 13 carried by the probe. The poles of the probe are placed against the surface of a test piece 14 of magnetic or electrically conductive material, but there are gaps 15 (show exaggerated) between the poles and the actual material of the test piece. When an alternating drive current $I_p$ is applied to the excitation coil 12, a first magnetic circuit is established through the probe 10, test piece 14 and gaps 15 in series. A second magnetic circuit parallel with the first is set up through the probe and the leakage path between the poles of the probe. An a-c voltage is induced in the pickup coil 13 and is proportional to the rate of change of the magnetic flux in the probe component of the parallel magnetic circuits. At any instant the magnetic flux in the probe component is equal to the sum of the flux in all the other magnetic circuit components. At any instant the magnetic field intensity in each component of the two magnetic circuits is related to the current $I_p$ applied to the excitation coil in the following manner:

$$N I_p = (HL)_{probe} + (HL)_{gaps} + (HL)_{testpiece}$$

$$N I_p = (HL)_{probe} + (HL)_{leakage}$$

in which
N = number of turns in excitation coil
H = respective field intensity
L = respective length of path.

Figure 2:
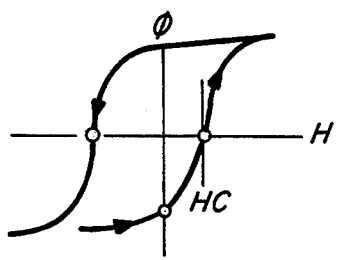
FIG. 2 is a curve illustrating a typical relation between the magnetic flux in a body of magnetic material and the intensity of the magnetic field in that body.

The curve of FIG. 2, which is the well known hysteresis loop, shows a typical relation between the magnetic flux and the intensity of the field induced in a body of magnetic material, such as magnetic components shown in FIG. 1 (probe and test piece). The ordinate $\phi$ represents the magnetic flux. The abscissa H represents the intensity of the magnetic field. The magnetic flux goes to zero twice during each full cycle of the magnetic field, but the field at the zero points of magnetic flux in general has positive and negative magnitudes not equal to zero. Hysteresis curves are also obtained when electrically conductive materials are exposed to alternating magnetic fields. However, in the nonmagnetic, non-conducting gaps the relation between the magnetic induction and field intensity is linear; that is, when the induction becomes zero, the field likewise becomes zero.

The relation between the current applied to the excitation coil and the time-integral of the a-c voltage induced in the pickup coil is similar to the relation between flux and field intensity for the probe material. An a-c voltage is induced in the pickup coil whenever the magnetic flux of the circuit is changing. The induced voltage can be integrated with respect to time to determine the flux in the probe. At two points in the a-c cycle the flux in the gaps is zero. Since the gaps are composed of non-conducting, linear or feebly magnetic material, the magnetic field intensity in the gaps at these points likewise is effectively zero, and the gaps have no effect on the magnetic circuit. Because of the hysteresis in the other magnetic circuit components, the field intensity in the other components is not zero and similarly the value of the current in the excitation coil at these points is not zero.

When the field intensity in the gaps becomes zero, analysis of the drive current in the excitation coil, controlled as hereinafter explained, eliminates the effects of the gaps and thereby affords a direct indication of the magnetic and/or electrical properties of the test piece and probe. If for a series of tests the probe is driven through identical magnetic flux cycles, the effect of the probe is constant. Therefore for identical magnetic flux cycles, variations in the value of the current in the excitation coil when the flux in the gaps is zero ($I_{PO}$) is related directly to the magnetic field intensity of the test piece. Different test pieces of course have different magnetic properties and produce different field intensities.

My invention utilizes this phenomenon to eliminate inaccuracies in magnetic testing caused by gaps in the magnetic circuit. As distinguished from the usual practice in which characteristics of the voltage induced in the pickup coil are analyzed to determine magnetic characteristics of the test piece, I control and analyze the drive current in the excitation coil with special well defined constraints on the magnetic flux in the gaps to make this determination.

In FIG. 1, block I shows schematically circuit components which generate a controlled drive current $I_P$ for the excitation coil 12. These components include an adder 18 and a power amplifier 19. A magnetic-flux reference signal voltage $V_R$ is applied to the adder 18 from a conventional oscillator signal generator (not shown). Preferably the signal has a saw-tooth wave form as indicated at 20. A signal $\phi_S$ representing the time-integral of the signal induced in the pickup coil 13 also is applied to the adder 18, as hereinafter explained, and the difference voltage or error signal ($V_R - \phi_S$) is transmitted from the adder to the power amplifier 19. The preferred operating mode is that $V_R$ and $\phi_S$ are nearly equal and the error signal is small. The power amplifier has a large gain and transmits a drive current $I_P$ via a resistor 21 to the excitation coil 12. A large signal gain in the power amplifier stage ensures that the error signal will be small.

In FIG. 1, block II shows schematically an electronic component 24 which integrates voltage $V_S$ from the pickup coil 13 to provide a signal $\phi_S$ directly related to the magnetic flux in the probe component of the circuit. Voltages are induced in the pickup coil in response to changes in the magnetic flux in the circuit (probe+-gaps+test piece). The instantaneous induced voltage in the pickup coil is proportaional to the time derivative of the magnetic flux in the probe, $d\phi/dt$. A signal proportional to the actual magnetic flux is needed. Therefore the integrating component 24 integrates the voltage with respect to time according to the formula:

$$\phi(S) = \int_{to}^{t} V_S \, dt.$$

This signal goes both to the adder 18 of block I and to components in a block III for eliminating d-c bias, as hereinafter explained.

In FIG. 1, block III shows schematically circuit components for eliminating d-c bias from the integrated induced voltage signal $\phi_S$. When the integration step is performed in block II, $t_o$ is arbitary and the axis about which the integrated voltage oscillates is not necessarily zero, as indicated at 26. The circuit components in block III include positive and negative peak detectors 27 and 28 and adders 29, 30 and 31. The integrated induced voltage signal $\phi_S$ goes to the two peak detectors and to the adder 29. The peak detectors 27 and 28 determine the positive and negative peaks respectively of the integrated induced voltage and transmit signals representative of $\phi_+$ and $\phi_-$ to adders 30 and 31. The adder 30 addes the two peak signals and divides the sum by two and thus determines the level of the d-c bias $\phi_{dc}$. The signal representing the d-c bias goes to the adder 29 which substracts the bias from the integrated induced voltage signal $\phi_S$ and thus determines $\phi$, the magnetic flux of the circuit, as indicated at 32. The adder 3 subtracts the negative peak signal $\phi_-$ from the positive peak signal $\phi_+$ to show the magnitude of the peak-to-peak magnetic flux $B_m$.

In FIG. 1, block IV shows circuit components which measure the actual drive current $I_P$ at the points of $\phi$ for which the flux in the gaps is zero. The components include first a buffer 35 which is connected in parallel with resistor 21 to receive a sample of the drive current $I_P$. The buffer provides isolation, and it extracts a signal proportional to $I_P$ without distortion. The signal from the buffer goes to the signal channel of a sample-and-hold component 36. The signal representing $\phi$ from the adder 29 goes to a comparator 37 which converts the saw tooth wave form to a square wave form, as indicated at 38. The signal form the comparator goes to the trigger input of the sample-and-hold component 36, where the square wave form furnishes a sharp leading edge for triggering the component to sample the current from the buffer 35.

In an ideal magnetic circuit which there is no leakage, the comparator 37 would compare the magnetic flux signal $\phi$ with zero volts as a reference to determine the condition of zero flux in the gaps and to provide the square wave signal 38. However, as already explained, there is a second magnetic circuit set up through the probe and a leakage path between the poles of the probe. Block IV preferably includes means which compensates for this leakage. Such means includes a connection 39 to transmit a leakage correction signal, which is proportional to the drive current from the buffer 35 to the comparator. The comparison corresponding to zero flux in the gaps thus is between the magnetic flux signal and the leakage correction signal as a reference, the leakage signal being proportional to the drive current.

Figure 3:
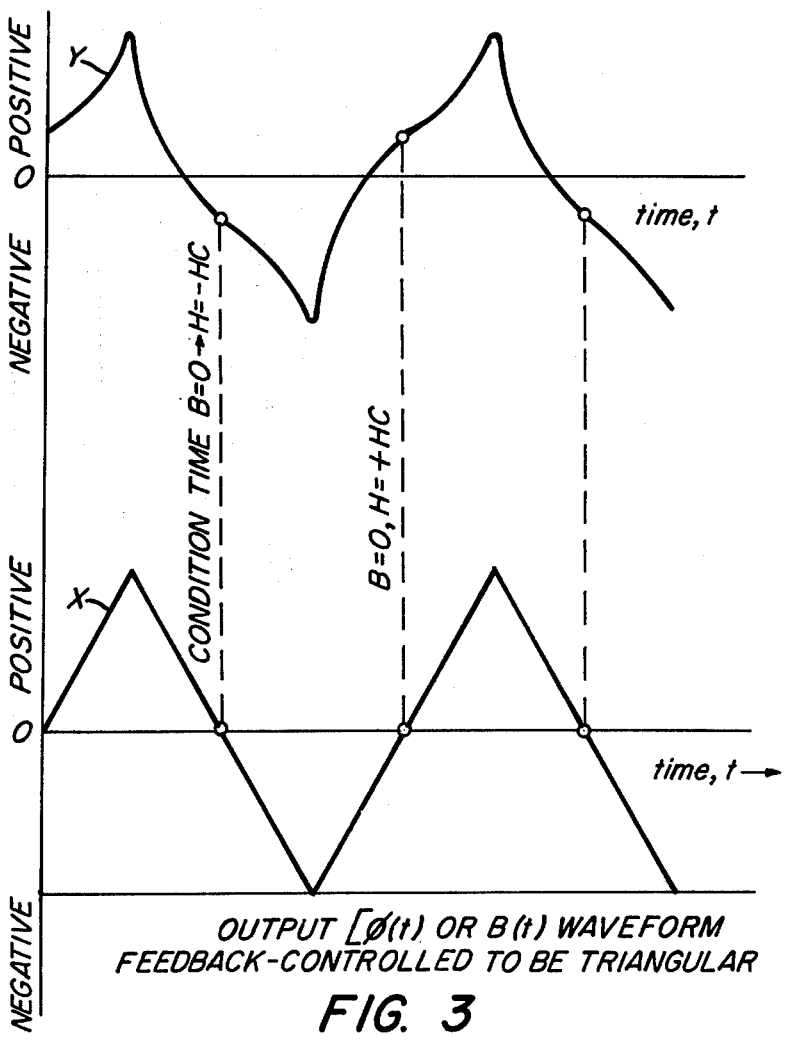
FIG. 3 is a pair of curves which show a typical phase relation between the flux induced in the magnetic circuit and the drive current in the excitation coil.

The curves of FIG. 3 illustrate a typical relation between the time integral of the voltage induced in the pickup coil $V_S$ and drive current $I_P$ in the excitation coil. In curve X I have plotted the magnetic flux or the time integral of the voltage $\phi_S$ induced in the pickup coil with respect to time. In curve Y I have plotted the drive current $I_P$ or the average magnetic field intensity with respect to time. Curve X shows a substantially uniform saw tooth wave form, and curve Y a somewhat distorted saw tooth wave form. At the zero voltage points on curve X, curve Y shows alternating positive and negative current magnitudes not zero. Analysis of this current indicates magnetic and electrical properties of the test piece.

The individual electronic components used in the invention method and apparatus are known circuits, versions of which are available commercially; hence I have not shown or described them in detail. However reference for circuit designs can be made to the publication:

J. G. Graeme, G. E. Tobey, and L. P. Huelsman, "Operational Amplifiers: Design and Applications", McGraw-Hill Book Company, New York, N.Y. 1971.

Some sources for commercially available versions of these circuits inlude Analog Devices, Inc., Norwood, Mass., Burr-Brown Research Corporation, Tucson, Ariz., Datel Systems, Inc. Canton, Mass.

From the foregoing description it is seen that my invention affords a simple and effective method and apparatus for magnetic testing and eliminating inaccuracies caused by gaps between the test instrument and the surface of the test piece. As distinguished from prior art, my invention controls the drive current to the excitation coil of the test instrument to produce a predetermined magnetic flux cycle in the magnetic circuit formed by the test piece and probe analyzes the drive current at points in the flux cycle which correspond to zero flux in the gaps, at which points the gaps have no effect on the measurement.

I claim:

1. In magnetic testing wherein a test probe carrying excitation and pickup coils is placed against a test piece of magnetic material forming magnetic circuits which comprise the probe, the test piece, flux leakage paths and gaps between the poles of the probe and the surface of the test piece, a-c voltage is applied to said excitation coil to provide a drive current, and an a-c voltage is induced in said pickup coil, an improved method of measuring magnetic and electrical properties of the test piece, comprising controlling the drive current to produce in the circuit a magnetic flux cycle of a predetermined wave form which becomes zero at points within the cycle, and analyzing the drive current at the zero points in the cycle.

2. A method as defined in claim 1 in which the voltage providing the drive current is obtained by amplifying an error signal obtained as the difference between a reference voltage and a signal representative of the magnetic flux.

3. A method as defined in claim 1 in which the zero points are determined by obtaining a signal representative of leakage between the poles of said probe, integrating the time derivative of the voltage induced in the pickup coil and comparing the integrated voltage with the signal representative of leakage as a reference.

4. A method as defined in claim 3 comprising a further step of eliminating d-c bias from the integrated voltage before comparing it with the reference.

5. In a magnetic testing apparatus which includes a double-pole probe, and excitation and pickup coils carried by said probe, an improved means for measuring magnetic properties of a test piece against which said probe is placed and eliminating inaccuracies in the test caused by gaps between the poles of the probe and the surface of the test piece, said improved means comprising means connected to said excitation coil for applying an a-c voltage thereto and providing a drive current therein of a magnitude to produce a magnetic flux in the magnetic circuit formed of the probe, test piece, leakage paths and gaps, and means for analyzing the magnitude of drive current at points in the time integral of the voltage induced in said pickup coil that correspond to zero flux in the gaps.

6. A magnetic testing apparatus as defined in claim 5 in which said means for applying an a-c voltage to said excitation coil includes means for supplying a reference a-c voltage, means for supplying an a-c voltage proportionate to the magnetic flux induced in the pickup coil, means connected to the two voltage supplying means for producing an error signal proportionate to the difference in the voltages supplied by each, and means for amplifying said error signal and transmitting it to said excitation coil.

7. A magnetic testing apparatus as defined in claim 6 in which the means for supplying voltage proportionate to the magnetic flux induced in the magnetic circuit includes means for integrating the time derivative of the voltage induced in the pickup coil.

8. A magnetic testing apparatus as defined in claim 5 comprising in addition means for eliminating d-c bias from the integrated voltage signal and for transmitting the integrated voltage signal without d-c bias to said means for analyzing the magnitude of drive current.

9. A magnetic testing apparatus as defined in claim 5 comprising in addition means connected to the means for providing drive current for compensating for flux leakage between the poles of said probe.

* * * * *

UNITED STATES PATENT AND TRADEMARK OFFICE
CERTIFICATE OF CORRECTION

PATENT NO. : 4,215,310
DATED : July 29, 1980
INVENTOR(S) : Frederick C. Schwerer, III It is certified that error appears in the above-identified patent and that said Letters Patent are hereby corrected as shown below:

Column 2, line 10, "show" should be -- shown --;

Column 2, line 4, "shows a diagrammatically" should be -- shows diagrammatically --;

Column 3, line 49, "proportaional" should be -- proportional --;

Column 4, line 6, "addes" should be -- adds --;

Column 4, line 11, "adder 3" should be -- adder 31 --;

Column 5, line 4, "inlude" should be -- include --.

Signed and Sealed this

Twenty-first Day of April 1981

[SEAL]

Attest:

RENE D. TEGTMEYER

Attesting Officer     Acting Commissioner of Patents and Trademarks